United States Patent [19]

Watanabe et al.

[11] Patent Number: 5,691,112
[45] Date of Patent: Nov. 25, 1997

US005691112A

[54] SULFONIUM SALT AND CHEMICALLY AMPLIFIED POSITIVE RESIST COMPOSITION

[75] Inventors: Satoshi Watanabe; Youichi Ohsawa; Toshinobu Ishihara; Kazumasa Maruyama; Yoshihumi Takeda; Junji Shimada, all of Niigata-ken; Fujio Yagihashi, Kanagawa; Katsuya Takemura, Niigata-ken, all of Japan

[73] Assignee: Shin-Etsu Chemical Co., Ltd., Tokyo, Japan

[21] Appl. No.: 762,861

[22] Filed: Dec. 10, 1996

Related U.S. Application Data

[62] Division of Ser. No. 379,986, Jan. 27, 1995, Pat. No. 5,633,409.

[30] Foreign Application Priority Data

| Jan. 28, 1994 | [JP] | Japan | 6-026171 |
| Mar. 29, 1994 | [JP] | Japan | 6-082359 |
| Apr. 8, 1994 | [JP] | Japan | 6-095560 |
| Nov. 28, 1994 | [JP] | Japan | 6-317626 |

[51] Int. Cl.$^6$ .................................................. G03F 7/004
[52] U.S. Cl. ................................................................. 430/270.1
[58] Field of Search ........................... 430/270.1; 568/49

[56] References Cited

FOREIGN PATENT DOCUMENTS

| 410 250 | 1/1991 | European Pat. Off. . |
| 615 163 | 9/1994 | European Pat. Off. . |

OTHER PUBLICATIONS

Chemical Abstract 123:325759.
Chemical Abstract 123:301551.
Chemical Registry, 157089–24–2.
Chemical Abstract of JP 6, 236, 036, vol. 122, No. 10, Mar. 6, 1995.

*Primary Examiner*—Christopher G. Young
*Attorney, Agent, or Firm*—Millen, White, Zelano & Branigan, P.C.

[57] ABSTRACT

Trifluoromethanesulfonic and p-toluenesulfonic acid bis- or tris(p-tert-butoxyphenyl)sulfonium salts are novel. They are prepared from bis(p-tert-butoxyphenyl)sulfoxide which is also novel. A chemically amplified positive resist composition which contains the sulfonium salt as a photo-acid generator is highly sensitive to deep-UV rays, electron beams and X-rays, can be developed with alkaline aqueous solution to form a pattern, and is thus suitable for use in a fine patterning technique.

7 Claims, No Drawings

SULFONIUM SALT AND CHEMICALLY AMPLIFIED POSITIVE RESIST COMPOSITION

This is a division, of the application Ser. No. 08/379,986 filed Jan. 27, 1995 U.S. Pat. No. 5,633,409.

BACKGROUND OF THE INVENTION

1. Field of the Invention

This invention relates to a novel sulfonium salt suitable for use in a chemically amplified, positive resist composition. It also relates to a chemically amplified, positive resist composition which is highly sensitive to high energy radiation such as deep-ultraviolet lights, electron rays and X-rays, can be developed with alkaline aqueous solution to form a pattern, and is thus suitable for use in a fine patterning technique. It also relates to novel bis(p-tert-butoxyphenyl) sulfoxide used as an intermediate in synthesizing the sulfonium salts.

2. Prior Art

As the LSI technology tends toward higher integration and high speed, further refinement of pattern rules is required. The current patterning technology mostly relies on light exposure which is now approaching to the essential limit of resolution which is dictated by the wavelength of a light source. It is generally recognized that in light exposure using g-line (wavelength 436 nm) or i-line (wavelength 365 nm) as a light source, a pattern rule of about 0.5 μm is the limit. For LSIs fabricated by such light exposure technique, a degree of integration equivalent to 16 mega-bit DRAM is the limit. At present, LSIs fabricated in the laboratory have reached this stage. It is urgently required to develop a finer patterning technique.

Under such circumstances, deep-ultraviolet lithography is regarded promising as the next generation of fine patterning technology. The deep-UV lithography is capable of working on the order of 0.3 to 0.4 μm. If a less light absorbing resist is used, it is possible to form a pattern having a side wall nearly perpendicular to the substrate. Great attention is now paid to the technique of utilizing a high illuminance KrF excimer laser as a deep-UV light source. In order to employ this technique on a mass production scale, a resist material having low light absorption and high sensitivity is desired.

From this point of view, a number of chemically amplified, positive working resist materials were recently developed using acid catalysts as disclosed in JP-B 27660/1990, JP-A 27829/1988, U.S. Pat. Nos. 4,491,628 and 5,310,619. These materials have high sensitivity, resolution and dry etching resistance and are promising as resist materials especially suited for deep-UV lithography.

It is known that the function of chemically amplified, positive resist materials is largely affected by photo-acid generators used therein. Typical photo-acid generators are onium salts as shown below.

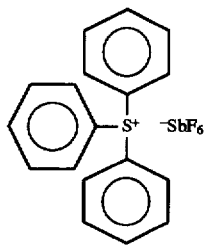

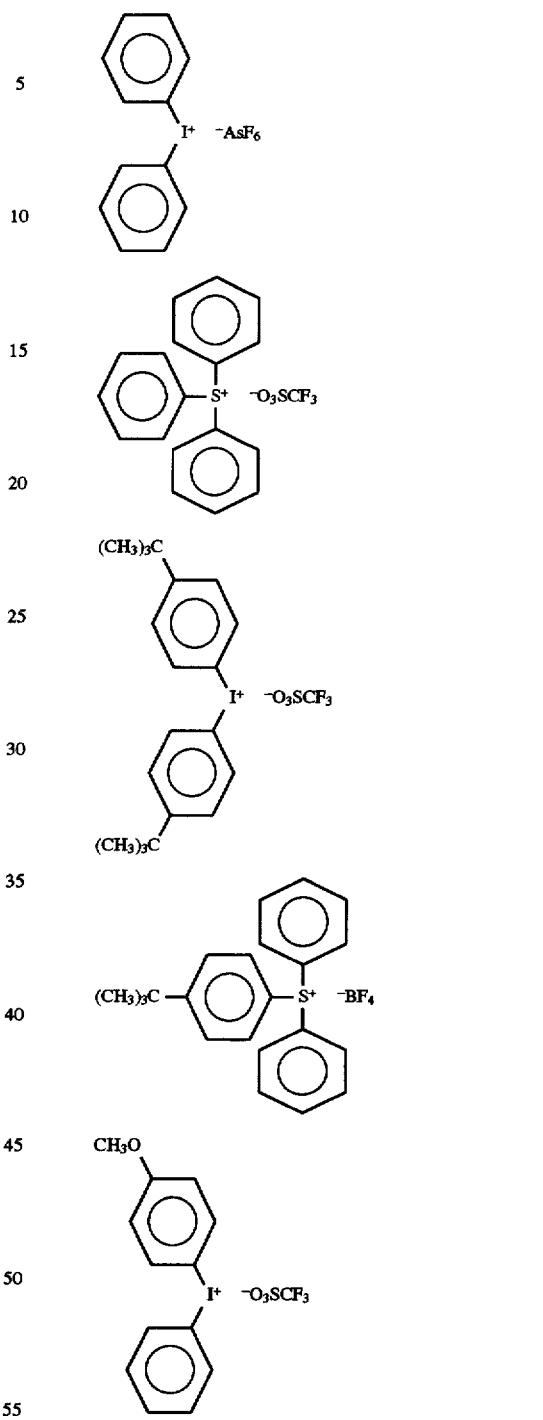

The onium salts themselves are oil soluble. When blended as a resist component, they act to reduce the solubility of the resist material in alkaline aqueous solution and to prevent the resist film from thinning upon development.

However, in exposed areas of positive resist material, photo-acid generators absorb high energy rays to decompose into products Which are also oil soluble. This reduces the rate of dissolution of the exposed areas in alkaline aqueous solution, failing to provide a high ratio of the alkali dissolution rate of exposed areas to that of unexposed areas (which ratio is known as dissolution contrast).

Consequently, chemically amplified, positive resists using onium salts as mentioned above are low in resolution upon alkaline development, that is, poor in removal of exposed areas, resulting in a pattern cross-sectional shape being upward tapered in trapezoid instead of a rectangular shape.

Prior art chemically amplified, positive resists, however, suffer from the problem known as post-exposure delay (PED) that when deep-UV, electron beam or X-ray lithography is carried out, line patterns would have a T-top configuration, that is, patterns become thick at the top if the leave-to-stand or delay time from exposure to post-exposure baking (PEB) is extended. This problem, which arises probably because the resist surface is reduced in solubility, becomes a serious drawback on practical application. This not only makes difficult dimensional control in the lithographic process, but also adversely affects dimensional control in the processing of substrates using dry etching. In this regard, reference is made to W. Hinsberg et al., J. Photopolym. Sce. Technol., 6 (4), 535–546 (1993) and T. Kumada et al., J. Photopolym., Sci. technol., 6 (4), 571–574 (1993). There are available no chemically amplified, positive resists which can resolve this problem and are thus practically acceptable.

It is understood that basic compounds in the air largely participate in the PED problem associated with chemically amplified, positive resists. Light exposure generates acids at the resist surface which react with basic compounds in the air and are thereby deactivated. As the delay time until PEB is extended, more amounts of acids are deactivated and accordingly, decomposition of acid labile groups are more unlikely to occur. As a consequence, an insolubilized layer is formed at the resist surface, resulting in a T-top configured pattern.

It is known from JP-A 232706/1993 and 249683/1993 that since addition of a basic compound suppresses the influence of basic compounds in the air, it is also effective for resolving the PED problem. However, the basic compound used therein is little taken into the resist film due to volatilization, less compatible with resist components, and unevenly dispersible in a resist film over its width. Thus the basic compound cannot achieve its advantages in a reproducible manner and causes a drop of resolving power.

SUMMARY OF THE INVENTION

Therefore, an object of the present invention is to provide a novel sulfonium salt suitable as a component of a chemically amplified, positive resist composition which has sufficiently high resolution to comply with a fine patterning technique. Another object of the invention is to provide an intermediate to he novel sulfonium salt. A further object of the invention is to provide a chemically amplified, positive resist composition containing such a sulfonium salt.

We have found that a novel sulfonium salt whose aromatic groups have substituted thereon at least two acid labile groups or tert-butoxy groups as represented by the general formula (1) can be prepared, for example, by reacting bis(p-tert-butoxyphenyl)sulfoxide of the general formula (3) with a trimethylsilyl-sulfonate compound of the general formula (4) and an aryl Grignard reagent of the following general formula (5) as shown below.

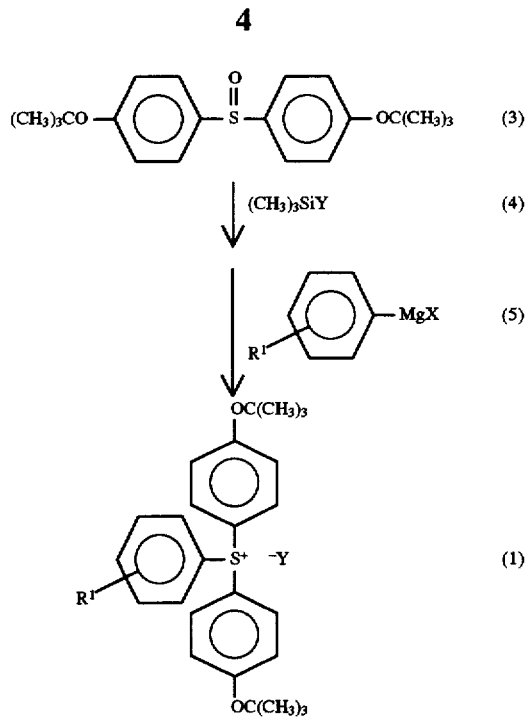

In the formulae, $R^1$ is a hydrogen atom, alkyl group or alkoxy group and Y is trifluoro-methanesulfonate or p-toluenesulfonate. This sulfonium salt is useful as a component of a chemically amplified, positive resist composition which has sufficiently high resolution to comply with a fine patterning technique. The composition is most effective when combined with deep-UV lithography.

Therefore, in a first aspect, the present invention provides a novel sulfonium salt of formula (1).

In a second aspect, the present invention provides bis(p-tert-butoxyphenyl)sulfoxide which is a novel intermediate used in the synthesis of a sulfonium salt of formula (1).

In a third aspect, the present invention provides a chemically amplified, positive resist composition comprising a sulfonium salt of formula (1).

In a preferred embodiment, a chemically amplified, positive resist composition includes (A) an organic solvent, (B) an alkali soluble resin, (C) a dissolution inhibitor having acid labile groups, (D) a sulfonium salt of formula (1), and (E) a photo-acid generator or an onium salt. In other preferred embodiments, the chemically amplified, positive resist composition includes components (A), (B), (C), and (D), or components (A), (B), and (D), or components (A), (B), (D), and (E).

The resist composition containing a sulfonium salt of formula (1) has several advantages. Due to the effect of acid labile groups in the sulfonium salt of formula (1), the resist composition has an enhanced dissolution contrast. Although the sulfonium salt of formula (1) itself is low soluble in alkali, it is decomposed to generate an acid upon exposure to high energy. By the action of this acid as well as post-exposure baking (PEB), tert-butoxy groups are efficiently decomposed to form a phenol derivative having high alkali solubility, which leads to an enhanced dissolution contrast. Therefore, the novel sulfonium salt of the invention exerts the full function as a photo-acid generator of a chemically amplified, positive resist composition, ensuring that the composition forms a resist image having a high degree of resolution and a wide range of focal depth.

DETAILED DESCRIPTION OF THE INVENTION

According to the present invention, a novel sulfonium salt has the general formula (1).

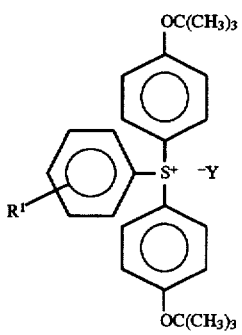
(1)

In formula (1), $R^1$ is a hydrogen atom, alkyl group or alkoxy group. Exemplary preferred alkyl groups are those having 1 to 8 carbon atoms, including methyl, ethyl, propyl, isopropyl, n-butyl, sec-butyl, tert-butyl, hexyl, and cyclohexyl groups, with the methyl, ethyl, isopropyl, and tert-butyl groups being especially preferred. Exemplary preferred alkoxy-groups are those having 1 to 8 carbon atoms, including methoxy, ethoxy, propoxy, isopropoxy, n-butoxy, sec-butoxy, tert-butoxy, hexyloxy, and cyclohexyloxy groups, with the methoxy, ethoxy, isopropoxy and tert-butoxy groups being especially preferred. Y is trifluoromethanesulfonate or p-toluenesulfonate.

More specifically, the sulfonium salts of the invention are represented by the following formulae (1a) and (1b).

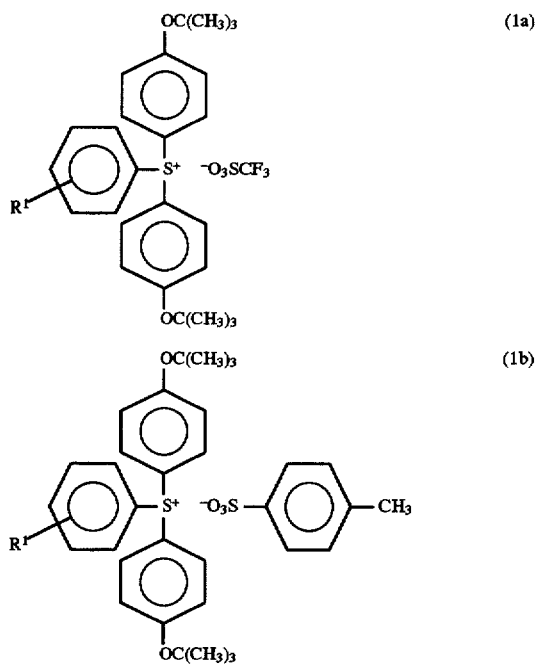

Particularly when a sulfonium salt of formula (1b) is used, the p-toluenesulfonate anion in the salt is effective for minimizing the influence of deactivation of acid at the resist surface by basic compounds in the air, formation of a surface insoluble layer is suppressed. The composition is then PED stable. Then the chemically amplified, positive resist composition containing the sulfonium salt solves the problem of an insoluble surface layer causing a T-top configuration, that is, the PED problem and has high sensitivity.

Several illustrative, non-limiting examples of the sulfonium salt of formula (1a) include trifluoromethanesulfonic acid bis(p-tert-butoxyphenyl)phenylsulfonium, trifluoromethanesulfonic acid bis(p-tert-butoxyphenyl) (p-methylphenyl)sulfonium, trifluoromethanesulfonic acid bis(p-tert-butoxyphenyl) (m-methylphenyl)sulfonium, trifluoromethanesulfonic acid bis(p-tert-butoxyphenyl) (o-methylphenyl)sulfonium, trifluoromethanesulfonic acid bis(p-tert-butoxyphenyl) (p-methoxyphenyl)sulfonium, trifluoromethanesulfonic acid bis(p-tert-butoxyphenyl) (m-methoxyphenyl)sulfonium, trifluoromethanesulfonic acid bis(p-tert-butoxyphenyl) (o-methoxyphenyl)sulfonium, triftuoromethanesulfonic acid tris(p-tert-butoxyphenyl) sulfonium, etc.

Several illustrative, non-limiting examples of the sulfonium salt of formula (1b) include p-toluenesulfonic acid bis(p-tert-butoxyphenyl)phenylsulfonium, p-toluenesulfonic acid bis(p-tert-butoxyphenyl)(p-methylphenyl)sulfonium, p-toluenesulfonic acid-bis(p-tert-butoxyphenyl)(m-methylphenyl)sulfonium, p-toluenesulfonic acid bis(p-tert-butoxyphenyl)(o-methylphenyl)sulfonium, p-toluenesulfonic acid bis(p-tert-butoxyphenyl)(p-methoxyphenyl) sulfonium, p-toluenesulfonic acid bis(p-tert-butoxyphenyl) (m-methoxyphenyl)sulfonium, p-toluenesulfonic acid bis(p-tert-butoxyphenyl) (o-methoxyphenyl)sulfonium, p-toluenesulfonic acid tris(p-tert-butoxy-phenyl)sulfonium, etc.

The sulfonium salt of formula (1) can be synthesized by reacting bis(p-tert-butoxyphenyl)sulfoxide of formula (3) with a trimethylsilylsulfonate compound of formula (4) and then with an aryl Grignard reagent of fermula (5) prepared in an organic solvent such as tetrahydrofuran (THF) according to the following reaction scheme.

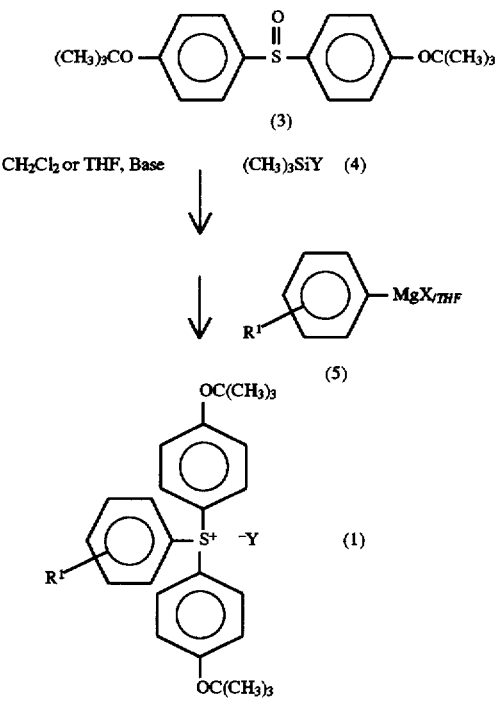

In the formulae, X is chlorine or bromine, $R^1$ and Y are as defined above.

This reaction is preferably carried out in an organic solvent such as methylene chloride and THF. In the first stage of reacting bis(p-tert-butoxyphenyl) sulfoxide of formula (3) with a trimethylsilylsulfonate compound of formula (4), the trimethylsilylsulfonate is desirably added dropwise in an amount of about 1 to 2 mol per mol of the sulfoxide compound of formula (3), more desirably in the presence of a base such as triethylamine and pyridine. Preferred reaction conditions include a temperature of about −78° C. to room temperature and a time of about 10 to 60 minutes.

in the second stage of reacting the intermediate with an aryl Grignard reagent of formula (5) prepared in an organic solvent such as THF, the aryl Grignard reagent is desirably added dropwise in an amount of about 1 to 3 mol per mol of the sulfoxide compound of formula (3) at a temperature of about −78° C. to room temperature. Stirring is continued at a temperature of about −10° C. to about 40° C. for about ½ to 2 hours. At the end of reaction, the solvent layer is washed with water and concentrated. The end sulfonium salt of formula (1) can be recovered by recrystallization or Icolumn fractionation.

Bis(p-tert-butoxyphenyl)sulfoxide of formula (3) can be synthesized by reacting a p-tert-butoxyphenyl Grignard reagent of formula (6) with thionyl chloride as shown below. Preferably the reaction is carried out in an organic solvent such as methylene chloride and THF.

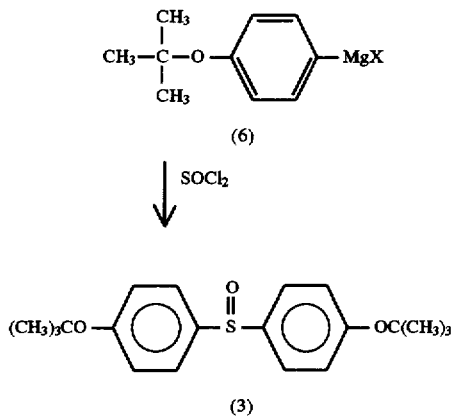

X is chlorine or bromine.

In reacting a Grignard reagent of formula (6) with thionyl chloride, the thionyl chloride is desirably added dropwise in an amount of about ⅙ to ½ mol, especially about ⅓ to ½ mol per mol of the Grignard reagent at a temperature of about −78° C. to 70° C., especially −60° C. to 10° C. over about 10 to 120 minutes, especially about 45 to 90 minutes. At the end of reaction, the solvent layer is washed with water, dried and concentrated. The end compound of formula (3) can be recovered by recrystallization or column chromatography.

With respect to the synthesis of sulfoxides from alkoxybenzenes and thionyl chloride in the presence of aluminum chloride, it is known in the art that a bis(p-alkoxyphenyl) sulfoxide, for example, bis(p-methoxyphenyl)sulfoxide is synthesized by reacting anisole with thionyl chloride in the presence of aluminum chloride. However, an attempt to synthesize the end compound of formula (3) by this process failed because tert-butoxy groups which are acid labile groups were decomposed by an acid generated during reaction and aluminum chloride which is a Lewis acid.

With respect to the synthesis of tert-butyl ether (tert-butoxyphenyl group) from aryl alcohol and isobutene, it is known that aryl alcohol reacts with isobutehe in the presence of an acid catalyst to form tert-butyl ether. However, when this process was applied to bis(p-hydroxyphenyl)sulfoxide, reaction did not proceed due to low solubility in a reaction medium such as methylene chloride and THF, failing. to produce. the end compound of formula (3). In this regard, reference is made to the literature, for example, Nikolenko and Krizhechkovskaya, J. Gen. Chem. USSR, 33, 3664 (1963), Smiles and Rossignol, J. Chem. Soc., 89, 696 (1906), and J. L. Holcombe and T. Livinghouse, J. Org. Chem., 51, 111–113 (1986).

Although the synthesis of sulfoxides from alkoxybenzenes and thionyl chloride in the presence of aluminum chloride invited cleavage of tert-butoxy groups due to an acid generated during reaction, we succeeded in synthesizing the end compound of formula (3), which could not be synthesized by the prior art processes, by adding dropwise thionyl chloride to a Grignard reagent whereby the reaction system could be always maintained alkaline to restrain cleavage of acid labile groups.

A chemically amplified, positive working resist composition is also contemplated herein. The composition contains a sulfonium salt of formula (1). The sulfonium salt serves as a photo-acid generator of a two component chemically amplified, positive resist composition consisting essentially of an alkali soluble resin and a photo-acid generator or a three component chemically amplified, positive resist composition consisting essentially of an alkali soluble resin, a photo-acid generator and a dissolution inhibitor. Preferably the sulfonium salt is added to a three component chemically amplified, positive resist composition as a photo-acid generator.

Preferably the resist composition is comprised of, in parts by weight, (A) 150 to 700 parts, more preferably 250 to 500 parts of an organic solvent, (B) 70 to 90 parts, more preferably 75 to 85 parts of an alkali soluble resin, (C) 5 to 40 parts, more preferably 10 to 25 parts of a dissolution inhibitor having acid labile groups, in the case of the three component system, (D) 1 to 15 parts, more preferably 2 to 8 parts of a sulfonium salt of formula (1), and optionally, (E) 0.5 to 15 parts, more preferably 2 to 8 parts of another photo-acid generator.

Examples of organic solvent (A) include ketones such as cyclohexanone and methyl-2-n-amylketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate and ethyl 3-ethoxypropionate, alone or in admixture of two or more. The most preferred solvent is 1-ethoxy-2-propanol because the acid generator of the resist composition is most soluble therein.

Examples of alkali soluble resin (B) include polyhydroxystyrene and derivatives thereof. Exemplary are those polyhydroxystyrene derivatives wherein hydrogen atoms of some OH groups of polyhydroxystyrene are replaced by acid labile groups and hydroxystyrene copolymers. For the polyhydroxystyrene derivatives, examples of the acid labile group used therein include tert-butyl, tert-butoxycarbonyl, tetrahydropyranyl, methoxy-methyl, trimethylsilyl, and tert-butyl dimethylsilyl groups, with the tert-butyl, tert-butoxycarbonyl, and tetrahydropyranyl groups being preferred. Exemplary hydroxystyrene copolymers include copolymers of hydroxystyrene and styrene, copolymers of hydroxystyrene and tert-butyl acrylate, copolymers of hydroxystyrene and tert-butyl methacrylate, copolymers of hydroxystyrene and maleic anhydride, and copolymers of hydroxystyrene and di-tert-butyl maleate. The polyhydroxystyrene and derivatives thereof should preferably have a weight average molecular weight of 5,000 to 100,000.

Dissolution inhibitor (C) should have at least one group which is decomposable with an acid (acid labile group) in a molecule and may be either a low molecular weight compound or a polymer. Any of well-known dissolution inhibitors may be used. Exemplary low molecular weight compounds include bisphenol A derivatives having acid labile groups and carbonate derivatives having acid labile groups, with those hisphenol A derivatives wherein OH groups of bisphenol A are replaced by t-butoxy or butoxycarbonyloxy groups being preferred. Examples of the polymeric dissolution inhibitor include copolymers of p-butoxystyrene and t-butyl acrylate, and copolymers of p-butoxy-styrene and maleic anhydride, with those copolymers having a weight average molecular weight of 500 to 10,000 being preferred.

Examples of photo-acid generator (E) include onium salts, oxime sulfonic acid derivatives, 2,6- dinitrobenzylsulfonic acid derivatives, diazonaphthoquinone sulfonate derivatives, 2,4-bistrichloromethyl-6-aryl-1,3,5-triazine derivatives, and α,α'-bisarylsulfonyl diazomethane derivatives. Preferred are onium salts of the following general formula (2):

$$(R^2)_n MY \qquad (2)$$

wherein $R^2$ is independently selected from substituted or unsubstituted aromatic groups, M is sulfonium or iodonium, Y is p-toluenesulfonate or trifluoromethanesulfonate, and letter n is equal to 2 or 3. Exemplary aromatic groups represented by $R^2$ are a phenyl group and phenyl groups having an alkyl or alkoxy substituent as described in formula (1).

Illustrative examples of the onium salt are given by the following iodonium and sulfonium salts.

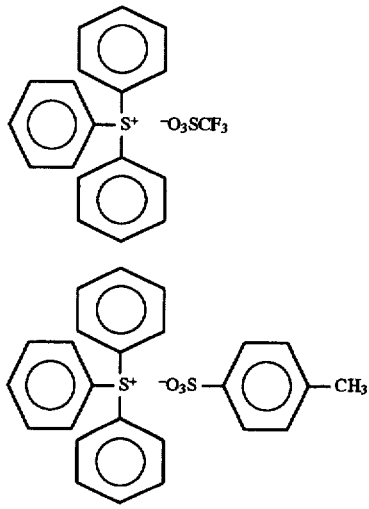

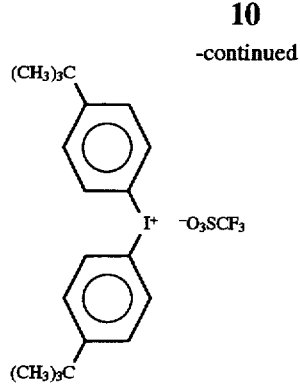

The resist composition of the invention may further contain a surfactant for improving coating properties and a light absorbing substance for reducing the influence of irregular reflection from the substrate.

With respect to the use of the resist composition of the invention and light exposure, any of well-known lithography techniques may be used. The resist composition of the invention is best suited for fine patterning using deep UV light of 254 to 193 nm and electron beams.

There has been described a novel sulfonium salt which serves as a photo-acid generator of a resist composition. Due to inclusion of at least two tert-butoxy groups which are acid labile groups, the sulfonium salt is effective for enhancing the dissolution contrast between exposed and unexpected areas. Then the sulfonium salt is an effective component of a chemically amplified, positive resist composition which has sufficiently high resolution to comply with a fine patterning technique. The resist composition containing a sulfonium salt of formula (1) is sensitive to high energy rays such as deep UV rays, electron beams and X-rays, especially KrF excimer laser beams as a positive resist material, can be patterned by development with alkaline aqueous solution, and has high sensitivity, resolution and resistance to plasma etching with the resulting resist pattern having improved heat resistance.

EXAMPLE

Examples of the present invention are given below by way of illustration and not by way of limitation.

Synthesis Example 1

Synthesis of bis(p-tert-butoxyphenyl)sulfoxide

A Grignard reagent was prepared in a conventional manner using 24.3 g (1 mol) of metallic magnesium, 203.2 g (1.1 mol) of p-tert-butoxyphenyl chloride and 280 g of THF. The Grignard reagent was diluted with 500 g of THF and cooled below –60° C. with a dry ice methanol bath. To the Grignard reagent solution, a solution of 47.5 g (0.4 mol) of thionyl chloride diluted with 70 g of THF was added dropwise over one hour at a temperature not exceeding 0° C. stirring was continued for one hour on the ice water bath and 36 g of water then added to decompose the excess of Grignard reagent. To the reaction solution were added 1000 g of methylene chloride, 400 g of saturated ammonium chloride aqueous solution and 300 g of water. After layer separation, the organic solvent layer was washed twice with 700 g of pure water. The organic solvent layer was dried over magnesium sulfate, filtered, and evaporated in vacuo. The resulting oily product was recrystallized, recovering 83 g (yield 60%) of the end product, bis(p-tert-butoxyphenyl)sulfoxide as a white crystal having a purity of 96% and a melting point of 80°–82° C.

The end product was analyzed by nuclear magnetic resonance (NMR) spectrometry, infrared (IR) spectrometry, and elemental analysis, with the results shown below.

Spectral data:

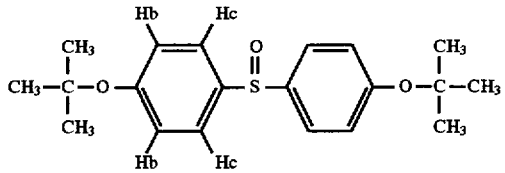

Proton NMR: CDCl$_3$, δ (ppm)

| 1.34 | Ha | singlet | 18H |
|---|---|---|---|
| 7.01–7.04 | Hb | doublet | 4H |
| 7.48–7.51 | Hc | doublet | 4H |

IR: (cm$^{-1}$)

2976, 2931, 1589, 1487, 1392, 1367, 1302, 1238, 1159, 1090, 1043, 1009, 930, 593, 852, 827

Elemental analysis (%) for $C_{20}H_{26}O_3S$

Calcd. C: 69.3 H: 7.6 N: —

Found C: 69.6 H: 7.7 N: —

Mass spectrum (m/z)

346 (M$^+$): 331,290 ($C_{20}H_{26}O_3S$=346)

mp: 80°–82° C.

Synthesis Example 2

Synthesis of trifluoromethanesulfonic acid bis(p-tert-butoxyphenyl)phenylsulfonium A solution of 40.0 g (0.12 mol) of bis(p-tert-butoxyphenyl)sulfoxide and 6.0 g (0.060 mol) of triethylamine in 400 g of methylene chloride was cooled to –70° C. with a dry ice methanol bath. With stirring, 28.4 g (0.13 mol) of (trimethylsilyl)trifluoromethanesulfonate, simply referred to as trimethylsilyltriflate, was added dropwise to the solution while controlling the temperature so as not to exceed –60° C.

Thereafter, the dry ice methanol bath was replaced by an ice water bath whereupon the reaction solution was stirred for 10 minutes at a reaction temperature of 0° to 5° C.

The reaction solution was cooled again to –70° C. with a dry ice methanol bath. A Grignard reagent which was prepared from 5.6 g (0.23 mol) of metallic magnesium, 60 g of THF and 26.0 g (0.23 mol) of chlorobenzene in a conventional manner was added dropwise to the solution while controlling the temperature so as not to exceed –60° C.

Thereafter, the dry ice methanol bath was replaced by an ice water bath whereupon the reaction solution was stirred for a further 60 minutes at a reaction temperature of 0° to 5° C., completing the reaction.

Water was added dropwise to the reaction solution to decompose the excess of Grignard reagent and the resulting inorganic salt was removed by filtration. The filtrate was washed three times with 520 g of water. The organic layer was evaporated in vacuo, obtaining an oily product. By recrystallization from the oily product, trifluoromethanesulfonic acid bis(p-tert-butoxyphenyl)phenylsulfonium was isolated in an amount of 16.8 g (yield 25%), a purity of 99%, and a melting point of 94°–96° C.

The end product was analyzed by NMR, IR spectrometry, and elemental analysis, with the results shown below.

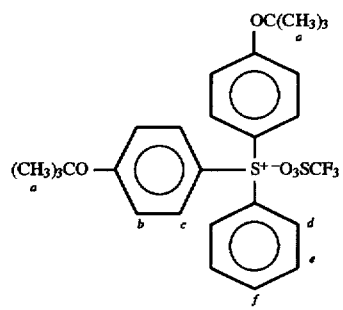

Proton NMR: CDCl$_3$, δ (ppm)

| (a) | 1.45 | singlet | 18H |
|---|---|---|---|
| (b) | 7.19–7.23 | doublet | 4H |
| (c)–(f) | 7.58–7.61 | multiplet | 9H |

IR: (cm$^{-1}$)

3066, 2981, 2937, 2875, 1585, 1489, 1446, 1396, 1371, 1309, 1265, 1223, 1157, 1072, 1030, 999, 928, 893, 839

Elemental analysis (%) for $C_{27}H_{33}F_3O_5S_2$

Calcd. C: 58.3 H: 5.6

Found C: 58.2 H: 5.6

Synthesis Example 3

Synthesis of trifluoromethanesulfonic acid tris(p-tert-butoxyphenyl)sulfonium With stirring and cooling on the cold bath, 37.8 g (0.17 mol) of trimethylsilyltriflate was added dropwise to a solution of 30.0 g (0.087 mol) of bis(p-tert-butoxyphenyl) sulfoxide and 13.4 g (0.17 mol) of pyridine in 200 g of THF while controlling the temperature so as not to exceed 0° C. The reaction solution was then stirred for 10 minutes at a reaction temperature of 0° to 5° C.

A Grignard reagent which was prepared from 4.2 g (0.17 mol) of metallic magnesium, 50 g of THF and 34.3 g (0.19 mol) of p-tert-butoxyphenyl chloride in a conventional manner was added dropwise to the reaction solution while controlling the temperature so as not to exceed 0° C. The reaction solution was then stirred for a further 60 minutes at a reaction temperature of 0° to 5° C., completing the reaction.

Water was added dropwise to the reaction solution to decompose the excess of Grignard reagent and the resulting inorganic salt was removed by filtration. To the filtrate, 600 g of methylene chloride, 300 g of saturated ammonium chloride aqueous solution and 400 g of water were added for separation. After layer separation, the organic layer was washed twice with 400 g of water. The organic layer was evaporated in vacuo, obtaining an oily product. By recrystallization from the oily product, trifluoromethanesulfonic acid tris(p-tert-butoxyphenyl)sulfonium was isolated in an amount of 27.3 g (yield 50%), a purity of 99%, and a melting point of 150°–152° C.

The end product was analyzed by NMR, IR spectrometry, and elemental analysis, with the results shown below.

Proton NMR: CDCl₃, δ (ppm)

[Structure: tris(p-tert-butoxyphenyl)sulfonium triflate, with labels a on OC(CH₃)₃ groups, b and c on aromatic protons]

| (a) | 1.42 | singlet | 27H |
| --- | --- | --- | --- |
| (b) | 7.17–7.20 | doublet | 6H |
| (c) | 7.55–7.59 | doublet | 6H |

IR: (cm⁻¹)
2980, 2937, 2875, 1585, 1490, 1417, 1396, 1371, 1309, 1269, 1267, 1223, 1159, 1076, 1030, 930, 908, 904, 839

Elemental analysis (%) for $C_{31}H_{39}F_3O_6S_2$

Calcd. C: 59.2 H: 6.2

Found C: 59.5 H: 6.4

Synthesis Example 4

Synthesis of trifluoromethanesulfonic acid bis(p-tert-butoxyphenyl)(p-methylphenyl)sulfonium

A solution of 40.0 g (0.12 mol) of bis(p-tert-butoxyphenyl)sulfoxide and 19.0 g (0.24 mol) of pyridine in 400 g of methylene chloride was cooled to −70° C. with a dry ice methanol bath. With stirring, 53.4 g (0.24 mol) of trimethylsilyltriflate was added dropwise to the solution while controlling the temperature so as not to exceed −60° C. Thereafter, the dry ice methanol bath was replaced by an ice water bath whereupon the reaction solution was stirred for 30 minutes at a reaction temperature of 0° to 5° C.

The reaction solution was cooled again to −70° C. with a dry ice methanol bath. A Grignard reagent which was prepared from 5.8 g (0.24 mol) of metallic magnesium, 60 g of THF and 30.4 g (0.24 mol) of 4-chlorotoluene in a conventional manner was added dropwise to the solution while controlling the temperature so as not to exceed −60° C. Thereafter, the dry ice methanol bath was replaced by an ice water bath whereupon the reaction solution was stirred for a further 60 minutes at a reaction temperature of 0° to 5° C., completing the reaction.

Water was added dropwise to the reaction solution to decompose the excess of Grignard reagent and the resulting inorganic salt was removed by filtration. To the filtrate were added 300 g of saturated ammonium chloride aqueous solution and 400 g of water. After layer separation, the organic layer was washed twice with 520 g of water. The organic layer was evaporated in vacuo, obtaining an oily product. The oily product was worked up by silica gel column chromatography, isolating trifluoromethanesulfonic acid bis(p-tert-butoxyphenyl) (p-methylphenyl)sulfonium in an amount of 26.7 g (yield 39%) and a purity of 98%.

The end product was analyzed by NMR, IR spectrometry, and elemental analysis, with the results shown below.

Proton NMR: CDCl₃, δ (ppm)

[Structure: bis(p-tert-butoxyphenyl)(p-methylphenyl)sulfonium triflate, with labels a on OC(CH₃)₃, b on CH₃, c, d, e, f on aromatic protons]

| (a) | 1.40 | singlet | 18H |
| --- | --- | --- | --- |
| (b) | 2.43 | singlet | 3H |
| (c)–(f) | 7.23–7.64 | multiplet | 12H |

IR: (cm⁻¹)
3065, 2980, 2935, 2875, 1584, 1489, 1446, 1395, 1371, 1310, 1265, 1223, 1157, 1073, 1030, 998, 927, 893, 840

Elemental analysis (%) for $C_{28}H_{33}F_3O_5S_2$

Calcd. C: 58.9 H: 5.8

Found C: 59.0 H: 5.6

Synthesis Example 5

Synthesis of p-toluenesulfonic acid bis(p-tert-butoxyphenyl) phenylsulfonium

With stirring and cooling on the cold bath, 24.4 g (0.1 mol) of (trimethylsilyl)-p-toluenesulfonate was added dropwise to a solution of 17.3 g (0.05 mol) of bis(p-tert-butoxyphenyl) sulfoxide and 10.1 g (0.1 mol) of triethylamine in 150 g of THF while controlling the temperature so as not to exceed 0° C. Thereafter, the reaction solution was stirred for 30 minutes at a reaction temperature of 0° to 5° C.

A Grignard reagent which was prepared from 2.4 g (0.1 mol) of metallic magnesium, 27 g of THF and 11.3 g (0.1 mol) of chlorobenzene in a conventional manner was added dropwise to the reaction solution while controlling the temperature so as not to exceed 0° C. Thereafter, the reaction solution was stirred for a further 60 minutes at a reaction temperature of 0° to 50° C., completing the reaction.

Water was added dropwise to the reaction solution to decompose the excess of Grignard reagent and the resulting inorganic salt was removed by filtration. To the filtrate were added 1000 g of methylene chloride and 700 g of saturated ammonium chloride aqueous solution. After layer separation, the organic layer was washed three times with 1000 g of water. The organic layer was evaporated in vacuo, obtaining an oily product. The oily product was worked up by silica gel column chromatography, isolating p-toluenesulfonic acid bis(p-tert-butoxyphenyl) phenylsulfonium in an amount of 8.8 g (yield 30%) and a purity of 98%.

The end product was analyzed by NMR, IR spectrometry, and elemental analysis, with the results shown below.

Proton NMR: CDCl₃, δ (ppm)

[Structure: triarylsulfonium tosylate with two (CH₃)₃CO-substituted phenyl groups, one unsubstituted phenyl, and p-toluenesulfonate counterion with CH₃-phenyl]

| | | | |
|---|---|---|---|
| (a) | 1.39 | singlet | 18H |
| (b) | 2.24 | singlet | 3H |
| (c) | 7.10–7.13 | doublet | 4H |
| (d)–(g) | 7.58–7.68 | multiplet | 9H |
| (h) | 7.75–7.78 | doublet | 2H |
| (i) | 6.99–7.02 | doublet | 2H |

IR: (cm⁻¹)

3059, 2978, 2933, 1583, 1489, 1446, 1265, 1203, 1201, 1159, 1119, 1072, 1034, 1012, 928, 895, 843, 816

Elemental analysis (%) for $C_{33}H_{22}O_5S_2$

Calcd. C: 68.5 H: 6.6

Found C: 68.3 H: 6.4

Synthesis Example 6

Synthesis of p-toluenesulfonic acid tris(p-tert-butoxyphenyl) sulfonium

With stirring and cooling on the cold bath, 14.2 g (0.058 mol) of (trimethylsilyl)-p-toluenesulfonate was added dropwise to a solution of 10.0 g (0.029 mol) of bis(p-tert-butoxyphenyl)sulfoxide and 5.8 g (0.058 mol) of triethylamine in 115 g of THF while controlling the temperature so as not to exceed 0° C. Thereafter, the reaction solution was stirred for 30 minutes at a reaction temperature of 0° to 5° C.

A Grignard reagent which was prepared from 1.4 g (0.058 mol) of metallic magnesium, 16 g of THF and 11.8 g (0.064 mol) of p-tert-butoxyphenyl chloride in a conventional manner was added dropwise to the reaction solution while controlling the temperature so as not to exceed 0° C. Thereafter, the reaction solution was stirred for a further 60 minutes at a reaction temperature of 0° to 5° C., completing the reaction.

Water was added dropwise to the reaction solution to decompose the excess of Grignard reagent and the resulting inorganic salt was removed by filtration. To the filtrate were added 600 g of methylene chloride, 200 g of saturated ammonium chloride aqueous solution and 200 g of water. After layer separation, the organic layer was washed three times with 500 g of water. The organic layer was evaporated in vacuo, obtaining an oily product. By recrystallization from the oily product, p-toluenesulfonic acid tris(p-tert-butoxyphenyl)sulfonium was isolated in an amount of 5.2 g (yield 28%), a purity of 99%, a melting point of 178° to 181° C.

The end product was analyzed by NMR, IR spectrometry, and elemental analysis, with the results shown below.

Proton NMR: CDCl₃, δ (ppm)

[Structure: triarylsulfonium tosylate with three (CH₃)₃CO-substituted phenyl groups and p-toluenesulfonate counterion with CH₃-phenyl]

| | | | |
|---|---|---|---|
| (a) | 1.39 | singlet | 27H |
| (b) | 2.25 | singlet | 3H |
| (c) | 7.10–7.13 | doublet | 6H |
| (d) | 7.63–7.66 | doublet | 6H |
| (e) | 7.79–7.82 | doublet | 2H |
| (f) | 7.02–7.05 | doublet | 2H |

IR: (cm⁻¹)

2978, 1583, 1489, 1369, 1307, 1263, 1261, 1217, 1200, 1159, 1120, 1074, 1034, 1012, 903, 897, 845, 816

Elemental analysis (%) for $C_{37}H_{45}O_6S_2$

Calcd. C: 68.3 H: 7.1

Found C: 68.2 H: 7.0

Synthesis Example 7

Synthesis of p-toluenesulfonic acid bis(p-tert-butoxyphenyl) (p-methylphenyl)sulfonium A solution 40.0 of g (0.12 mol) of bis(p-tert-butoxyphenyl)sulfoxide and 19.0 g (0.24 mol) of pyridine in 400 g of methylene chloride was cooled at −70° C. with a dry ice methanol bath. With stirring, 58.7 g (0.24 mol) of (trimethylsilyl)-p-toluenesulfonate was added dropwise to the solution while controlling the temperature so as not to exceed −60° C. Thereafter, the dry ice methanol bath was replaced by an ice water bath whereupon the reaction solution was stirred for 30 minutes at a reaction temperature of 0° to 5° C.

The reaction solution was cooled again to −70° C. with a dry ice methanol bath. A Grignard reagent which was prepared from 5.8 g (0.24 mol) of metallic magnesium, 60 g of THF and 30.4 g (0.24 mol) of 4-chlorotoluene in a conventional manner was added dropwise to the reaction solution while controlling the temperature so as not to exceed −60° C. Thereafter, the dry ice methanol bath was replaced by an ice water bath whereupon the reaction solution was stirred for a further 60 minutes at a reaction temperature of 0° to 5° C., completing the reaction.

Water was added dropwise to the reaction solution to decompose the excess of Grignard reagent and the resulting inorganic salt was removed by filtration. To the filtrate were added 300 g of saturated ammonium chloride aqueous solution and 400 g of water. After layer separation, the organic layer was washed twice with 520 g of water. The organic layer was evaporated in vacuo, obtaining an oily product. The oily product was worked up by silica gel column chromatography, isolating p-toluenesulfonic acid bis(p-tert-butoxyphenyl)(p-methylphenyl) sulfonium in an amount of 24.9 g (yield 35%) and a purity of 98%.

The end product was analyzed by NMR, IR spectrometry, and elemental analysis, with the results shown below.

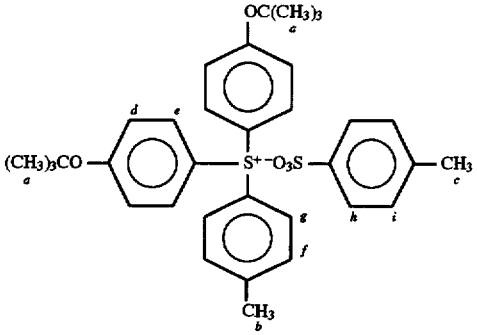

Proton NMR: CDCl₃, δ (ppm)

| | | | |
|---|---|---|---|
| (a) | 1.39 | singlet | 18H |
| (b) | 2.43 | singlet | 3H |
| (c) | 2.25 | singlet | 3H |
| (d)–(i) | 7.02–7.82 | multiplet | 16H |

IR: (cm$^{-1}$)
3060, 2978, 2932, 1583, 1488, 1447, 1396, 1369, 1307, 1265, 1204, 1201, 1159, 1118, 1072, 1034, 1012, 928, 895, 843, 815

Elemental analysis (%) for $C_{34}H_{40}O_5S_2$
Calcd. C: 68.9 H: 6.8
Found C: 68.8 H: 6.8

Examples 1–11 and Comparative Examples 1–4

Liquid resist compositions were prepared by dissolving a polyhydroxystyrene derivative of the following formula Polym. 1 wherein some OH groups are protected by t-butoxycarbonyl groups, a polyhydroxystyrene derivative of the following formula Polym. 2 wherein some OH groups are protected by t-butyl groups, or a polyhydroxystyrene derivative of the following formula Polym. 3 wherein some OH groups are protected by tetrahydropyranyl groups, a photo-acid generator selected from the sulfonium and onium salts of the formulae PAG. 1 to PAG. 5, and a dissolution inhibitor in the form of 2,2'-bis(4-tert-butoxycarbonyloxyphenyl)propane of the formula DRI. 1, in 1-ethoxy-2-propanol (EtOIA) in accordance with the formulation shown in Table 1.

Each of the compositions was passed through a 0.2-μm Teflon® filter. It was then spin coated onto a silicon wafer to form a coating of 0.8 μm thick. With the silicon wafer rested on a hot plate at 100° C., the coating was pre-baked for 120 seconds.

The film was exposed to a pattern of light by means of an excimer laser stepper model NSR 2005EX (manufactured by Nikon K.K., numerical aperture NA=0.5), baked at 90° C. for 60 seconds, and developed with an aqueous solution of 2.38% tetramethylammonium hydroxide, obtaining a positive pattern.

The resulting resist pattern was evaluated as follows.

First, sensitivity (Eth value) was determined. Provided that the exposure quantity with which the top and bottom of a 0.35-μm line-and-space pattern were resolved at 1:1 was the optimum exposure, the minimum line width of a line-and-space pattern which was recognized separate at this exposure was the resolution of a test resist. The configuration of the resist pattern resolved was observed under a scanning electron microscope.

The results are shown in Table 1.

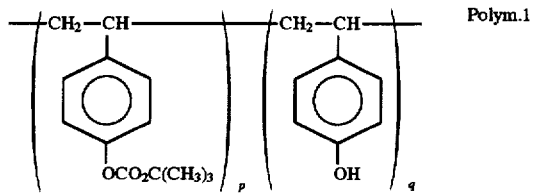

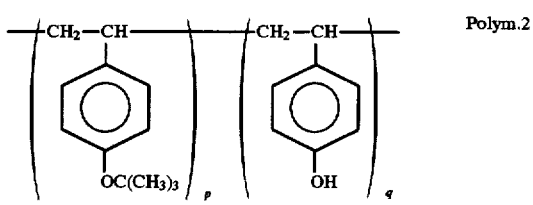

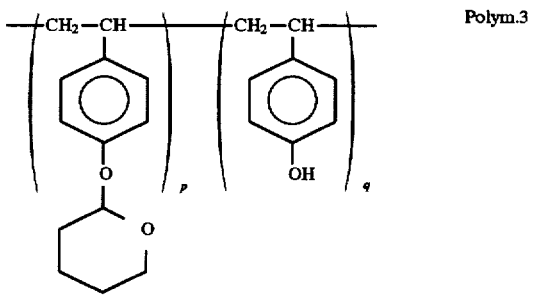

p/(p+q)=0.1–0.3 weight average molecular weight 10,000–50,000

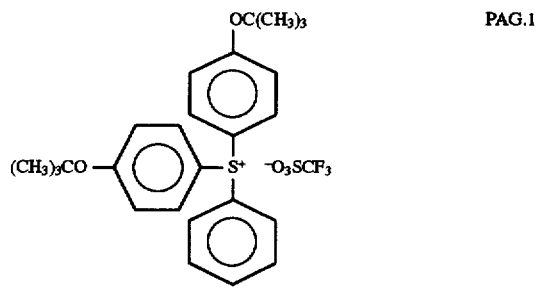

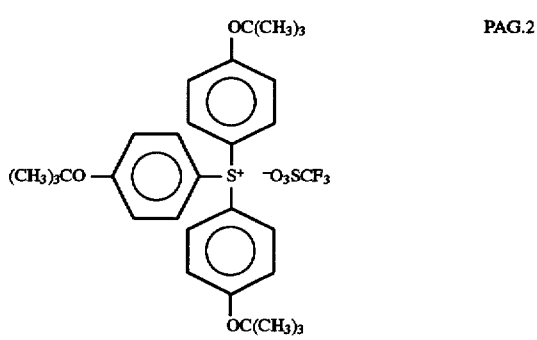

-continued

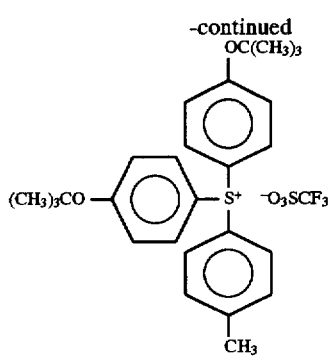
PAG.3

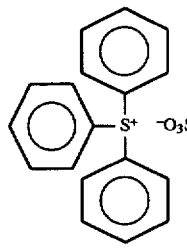

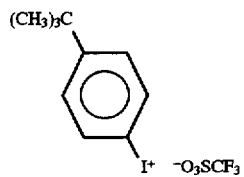

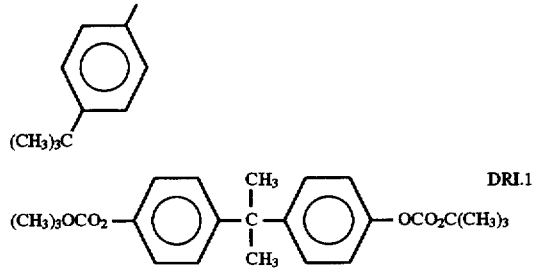
DRI.1

Examples 12–22 and Comparative Examples 5–8

Positive patterns were formed by the same procedure as in Example 1 except that the photo-acid generator is selected from PAG. 6 to PAG. 8 and PAG. 4 and PAG. 5.

The resulting resist pattern was evaluated as follows.

First, sensitivity (Eth value) was determined. Provided that the exposure quantity with which the top and bottom of a 0.35-μm line-and-space pattern were resolved at 1:1 was the optimum exposure, the minimum line width of a line-and-space pattern which was recognized separate at this exposure was the resolution of a test resist. The configuration of the resist pattern resolved was observed under a scanning electron microscope. The resist was determined for PED stability by exposing at the optimum exposure, leaving the resist film to stand for a varying time, and baking the film. The delay time was determined at which a change in the resist pattern configuration was observed, for example, the line pattern was T-top configured or resolution became impossible. The longer the delay time, the better is the PED stability.

The results are shown in Table 2.

PAG.4

PAG.5

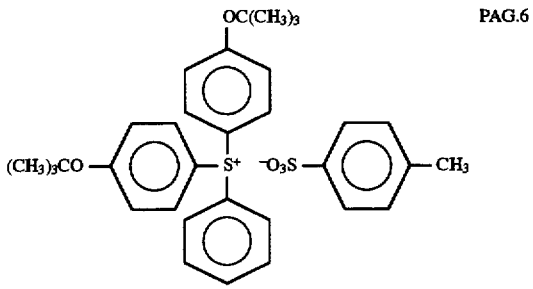
PAG.6

TABLE 1

| Example | Resist composition (pbw) Alkali soluble resin | Photo-acid generator | Dissolution inhibitor | Solvent | Sensitivity Eop (mJ/cm²) | Resolution (μm) | Pattern shape |
|---|---|---|---|---|---|---|---|
| E1 | Polym.1 (75) | PAG.1 (5) | DRI.1 (20) | EtOIPA (450) | 4.0 | 0.22 | rectangular |
| E2 | Polym.2 (75) | PAG.2 (5) | DRI.1 (20) | EtOIPA (450) | 4.0 | 0.22 | rectangular |
| E3 | Polym.3 (75) | PAG.3 (5) | DRI.1 (20) | EtOIPA (450) | 5.5 | 0.24 | rectangular |
| E4 | Polym.1 (70) | PAG.1 (2) PAG.4(2) | DRI.1 (20) | EtOIPA (500) | 4.0 | 0.28 | rectangular |
| E5 | Polym.2 (70) | PAG.1 (2) PAG.5(2) | DRI.1 (20) | EtOIPA (500) | 4.0 | 0.25 | rectangular |
| E6 | Polym.3 (70) | PAG.1 (2) PAG.5(2) | DRI.1 (20) | EtOIPA (500) | 5.0 | 0.25 | rectangular |
| E7 | Polym.1 (70) | PAG.3 (3) PAG.5(2) | DRI.1 (10) | EtOIPA (400) | 4.0 | 0.25 | rectangular |
| E8 | Polym.2 (70) | PAG.3 (3) PAG.4(2) | DRI.1 (10) | EtOIPA (400) | 4.5 | 0.28 | rectangular |
| E9 | Polym.3 (70) | PAG.3 (3) PAG.4(2) | DRI.1 (10) | EtOIPA (400) | 5.0 | 0.28 | rectangular |
| E10 | Polym.1 (80) | PAG.2 (6) | — | EtOIPA (400) | 4.5 | 0.28 | rectangular |
| E11 | Polym.1 (80) | PAG.2 (4) PAG.4(2) | — | EtOIPA (400) | 5.0 | 0.30 | rectangular |
| CE1 | Polym.1 (75) | PAG.4 (5) | DRI.1 (20) | EtOIPA (450) | 4.0 | 0.35 | somewhat upward tapered |
| CE2 | Polym.2 (75) | PAG.5 (5) | DRI.1 (20) | EtOIPA (450) | 4.0 | 0.30 | somewhat upward tapered |
| CE3 | Polym.3 (75) | PAG.5 (5) | DRI.1 (20) | EtOIPA (450) | 4.0 | 0.30 | upward tapered |
| CE4 | Polym.1 (80) | PAG.4 (6) | — | EtOIPA (400) | 5.5 | 0.40 | upward tapered |

-continued

PAG.7

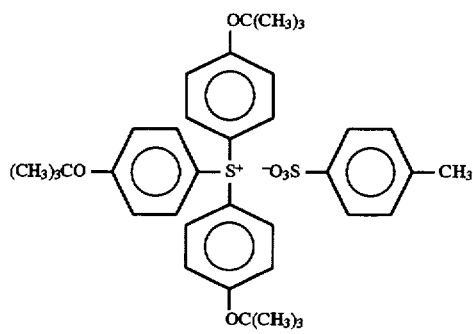

PAG.8

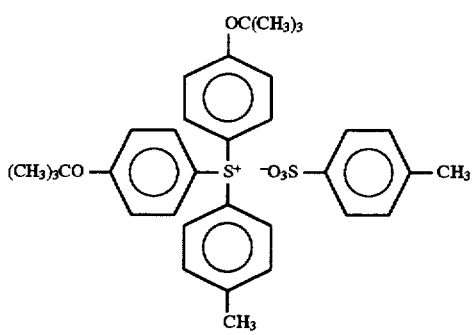

Reference Example

Synthesis of trifluoromethanesulfonic acid bis(p-tert-butoxyphenyl)(p-dimethylaminophenyl) sulfonium A solution of 8.5 g (0.025 mol) of bis(p-tert-butoxyphenyl)sulfoxide and 1.3 g (0.013 mol) of triethylamine in 110 g of methylene chloride was cooled to −70° C. with a dry ice methanol bath. With stirring, 6.0 g (0.027 mol) of trimethylsilyltriflate was added dropwise to the solution while controlling the temperature so as not to exceed −60° C. Thereafter, the dry ice methanol bath was replaced by an ice water bath whereupon the reaction solution was stirred for 10 minutes at a reaction temperature of 0° to 5° C.

The reaction solution was cooled again to −70° C. with a dry ice methanol bath. A Grignard reagent which was prepared from 1.2 g (0.049 mol) of metallic magnesium, 18.9 g of THF and 9.9 g (0.049 mol) of 4-bromo-N,N-dimethylaniline in a conventional manner was added dropwise to the solution while controlling the temperature so as not to exceed −60° C. Thereafter, the dry ice methanol bath was replaced by an ice wager bath whereupon the reaction solution was stirred for a further 60 minutes at a reaction temperature of 0° to 5° C., completing the reaction.

Water was added dropwise to the reaction solution to decompose the excess of Grignard reagent and the resulting inorganic salt was removed by filtration. The filtrate was washed three times with 130 g of water. The organic layer was evaporated in vacuo, obtaining an oily product. The oily product was worked up by silica gel column chromatography, isolating trifluoromethanesulfonic acid bis (p-tert-butoxyphenyl) (p-dimethylaminophenyl)sulfonium in an amount of 4.8 g (yield 32%) and a purity of 98%.

The end product was analyzed by NMR, IR spectrometry, and elemental analysis, with the results shown below.

TABLE 2

| Example | Resist composition (bpw) | | | | Sensitivity Eop (mJ/cm$^2$) | Resolution (μm) | Pattern shape | PED stability (min.) |
| --- | --- | --- | --- | --- | --- | --- | --- | --- |
| | Alkali soluble resin | Photo-acid generator | Dissolution inhibitor | Solvent | | | | |
| E12 | Polym.1 (80) | PAG.6 (5) | DRI.1 (20) | EtOIPA (450) | 13.0 | 0.22 | rectangular | ≧60 |
| E13 | Polym.2 (80) | PAG.7 (5) | DRI.1 (20) | EtOIPA (450) | 13.0 | 0.22 | rectangular | ≧60 |
| E14 | Polym.3 (80) | PAG.8 (5) | DRI.1 (20) | EtOIPA (450) | 18.0 | 0.24 | rectangular | ≧60 |
| E15 | Polym.1 (75) | PAG.6 (2) PAG.4 (2) | DRI.1 (20) | EtOIPA (500) | 11.0 | 0.28 | rectangular | ≧30 |
| E16 | Polym.2 (75) | PAG.6 (2) PAG.5 (2) | DRI.1 (20) | EtOIPA (500) | 10.0 | 0.25 | rectangular | ≧30 |
| E17 | Polym.3 (75) | PAG.6 (2) PAG.5 (2) | DRI.1 (20) | EtOIPA (500) | 14.0 | 0.28 | rectangular | ≧30 |
| E18 | Polym.1 (75) | PAG.8 (3) PAG.5 (2) | DRI.1 (10) | EtOIPA (400) | 12.0 | 0.25 | rectangular | ≧30 |
| E19 | Polym.2 (70) | PAG.8 (3) PAG.4 (2) | DRI.1 (10) | EtOIPA (400) | 12.0 | 0.25 | rectangular | ≧30 |
| E20 | Polym.3 (70) | PAG.8 (3) PAG.4 (2) | DRI.1 (10) | EtOIPA (400) | 14.0 | 0.28 | rectangular | ≧30 |
| E21 | Polym.1 (80) | PAG.7 (6) | — | EtOIPA (400) | 10.0 | 0.28 | rectangular | ≧30 |
| E22 | Polym.1 (80) | PAG.7 (4) PAG.4 (2) | — | EtOIPA (400) | 11.0 | 0.30 | rectangular | ≧30 |
| CE5 | Polym.1 (75) | PAG.4 (5) | DRI.1 (20) | EtOIPA (450) | 4.0 | 0.35 | somewhat upward tapered | ≦5 |
| CE6 | Polym.2 (75) | PAG.5 (5) | DRI.1 (20) | EtOIPA (450) | 4.0 | 0.30 | somewhat upward tapered | ≦5 |
| CE7 | Polym.3 (75) | PAG.5 (5) | DRI.1 (20) | EtOIPA (450) | 4.0 | 0.30 | upward tapered | ≦5 |
| CE8 | Polym.1 (80) | PAG.4 (6) | — | EtOIPA (400) | 5.5 | 0.40 | upward tapered | ≦5 |

Proton NMR: CDCl₃, δ (ppm)

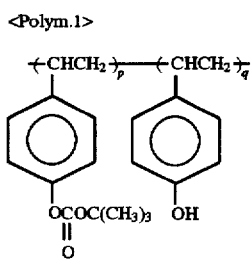

| | | | |
|---|---|---|---|
| (a) | 1.38 | singlet | 18H |
| (b) | 3.00 | singlet | 6H |
| (c) | 6.76–6.79 | doublet | 2H |
| (e) | 7.11–7.15 | doublet | 4H |
| (d), (f) | 7.40–7.45 | multiplet | 6H |

IR: (cm⁻¹)

3095, 3072, 2980, 2935, 2873, 2827, 1589, 1520, 1489, 1446, 1373, 1308, 1265, 1223, 1203, 1157, 1074, 1030, 991, 927, 892, 816

Elemental analysis (%) for $C_{29}H_{36}F_3NO_5$

Calcd. C: 58.1 H: 6.0 N: 2.3

Found C: 57.8 H: 6.3 N: 2.2

A liquid resist composition was prepared by dissolving 80 parts by weight of a polyhydroxystyrene derivative of the following formula Polym. 1 wherein some OH groups are protected by t-butoxycarbonyl groups, 3 parts by weight of the above-prepared trifluoromethanesulfonic acid bis(p-tert-butoxyphenyl)(p-dimethylaminophenyl)sulfonium, and 20 parts by weight of a dissolution inhibitor 2,2'-bis(4-tert-butoxycarbonyloxyphenyl)propane of the formula DRI. 1 in 450 parts by weight of 1-ethoxy-2-propanol.

<Polym.1>

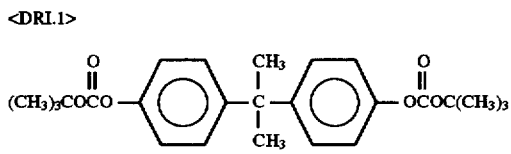

weight average molecular weight 10,000–50,000 p/(p+q)= 0.1–0.3

<DRI.1>

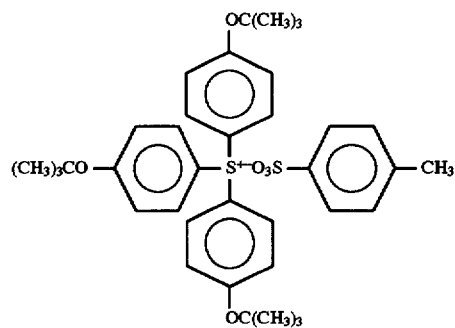

The composition was passed through a 0.2-μm Teflon® filter. It was then spin coated onto a silicon wafer to form a coating of 0.1 μm thick. With the silicon wafer rested on a hot plate at 100° C., the coating was pre-baked for 120 seconds.

The film was exposed to a pattern of light by means of an excimer laser stepper model NSR 2005EX (manufactured by Nikon K.K., NA=0.5), baked at 90° C. for 60 seconds, and developed with an aqueous solution of 2.38% tetramethylammonium hydroxide, obtaining a positive pattern.

The resulting resist pattern was evaluated as follows.

First, sensitivity (Eth value) was determined. Provided that the exposure quantity with which the top and bottom of a 0.4-μm line-and-space pattern were resolved at 1:1 was the optimum exposure, the minimum line width of a line-and-space pattern which was recognized separate at this exposure was the resolution of a test resist. The configuration of the resist pattern resolved was observed under a scanning electron microscope. The resist was determined for PED stability by exposing at the optimum exposure, leaving the resist film to stand for a varying time, and baking the film. The leave-to-stand time was determined at which a change in the resist pattern configuration was observed, for example, the line pattern was T-top configured or resolution became impossible. The longer the leave-to-stand time, the better is the PED stability.

The resist showed a sensitivity of 115.0 mJ/cm², a resolution of 0.28 μm, a good pattern shape, and a PED stability of at least 120 minutes.

Japanese Patent Application Nos. 6-26171, 6-82359 and 6-95560 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A chemically amplified, positive resist composition comprising a sulfonium salt of formula (1)

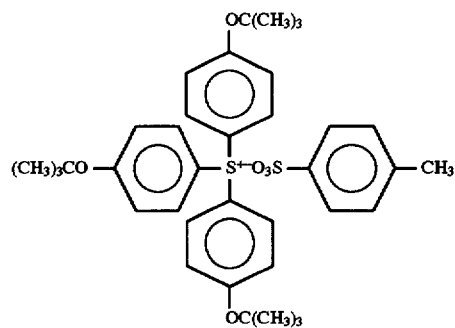

2. A chemically amplified, positive resist composition comprising (A) an organic solvent, (B) an alkali soluble resin, (C) a dissolution inhibitor having an acid labile group, (D) a sulfonium salt of formula (1) as set forth in claim 1, and (E) a photo-acid generator.

3. A chemically amplified, positive resist composition comprising (A) an organic solvent, (B) an alkali soluble resin, (C) a dissolution inhibitor having acid labile groups, (D) a sulfonium salt of formula (1) as set forth in claim 1, and (E) an onium salt of the following general formula (2):

$$(R^2)_n MY \qquad (2)$$

wherein $R^2$ is independently selected from substituted or unsubstituted aromatic groups, M is sulfonium or iodonium, Y is trifluoromethanesulfonate or p-toluenesulfonate, and letter n is equal to 2 or 3.

4. A chemically amplified, positive resist composition comprising (A) an organic solvent, (B) an alkali soluble resin, (C) a dissolution inhibitor having an acid labile group, and (D) a sulfonium salt of formula (1) as set forth in claim 1.

5. A chemically amplified, positive resist composition comprising (A) an organic solvent, (B) an alkali soluble resin, and (D) a sulfonium salt of formula (1) as set forth in claim 1.

6. A chemically amplified, positive resist composition comprising (A) an organic solvent, (B) an alkali soluble resin, (D) a sulfonium salt of formula (1) as set forth in claim 1, and (E) a photo-acid generator.

7. The composition of claim 2 wherein said alkali soluble resin (B) is a polyhydroxystyrene in which hydrogen atoms of some hydroxyl groups are replaced by acid labile groups and which has a weight average molecular weight of 5,000 to 100,000.

* * * * *